United States Patent [19]

Permenter et al.

[11] Patent Number: 4,795,443

[45] Date of Patent: Jan. 3, 1989

[54] SYRINGE SEALING DEVICE AND METHOD

[75] Inventors: L. Michael Permenter, Acworth; Richard W. Beckham, Martinez, both of Ga.

[73] Assignee: Peachtree Medical, Inc., Marietta, Ga.

[21] Appl. No.: 39,460

[22] Filed: Apr. 16, 1987

[51] Int. Cl.⁴ ............................................. A61M 5/00
[52] U.S. Cl. .................................... 604/198; 604/263
[58] Field of Search ...................... 604/110, 192–199, 604/263; 128/760, 762, 764, 765, 766; 401/104–108, 98, 202, 213, 243–247, 262, 269; 206/364, 365, 367

[56] References Cited

U.S. PATENT DOCUMENTS

| 1,876,461 | 9/1932 | Kutter | 401/108 |
|---|---|---|---|
| 2,677,374 | 5/1954 | Burnside | 128/218 |
| 2,700,385 | 1/1955 | Ortiz | 604/263 |
| 2,831,483 | 4/1958 | De Lorenzo | 604/192 |
| 2,854,976 | 10/1958 | Heydrich | 604/263 |
| 2,922,395 | 1/1960 | De Baun | 401/243 |
| 3,370,588 | 2/1968 | Burke | 604/192 |
| 3,378,007 | 4/1968 | Poulsen | 128/220 |
| 3,513,830 | 5/1970 | Kalayzian | 604/192 |
| 3,658,061 | 4/1972 | Hall | 604/263 |
| 3,992,115 | 11/1976 | Culver | 401/213 |
| 4,043,334 | 8/1977 | Brown et al. | 128/215 |
| 4,106,031 | 8/1978 | Jozat | 401/107 |
| 4,248,246 | 2/1981 | Ikeda | 604/263 |
| 4,329,989 | 5/1982 | Pallons et al. | 604/192 |
| 4,356,822 | 11/1982 | Winstead-Hall | 128/215 |
| 4,573,976 | 3/1986 | Sampson et al. | 604/263 |
| 4,631,057 | 12/1986 | Mitchell | 604/198 |
| 4,659,330 | 4/1987 | Nelson et al. | 604/263 |

FOREIGN PATENT DOCUMENTS 103966 8/1926 Austria ............................ 604/263

Primary Examiner—Stephen C. Pellegrino
Assistant Examiner—Ralph Lewis
Attorney, Agent, or Firm—Thomas & Kennedy

[57] ABSTRACT

A device for sealing the tip of a syringe needle has a cap from which a shank extends to a mount adapted to be slidably held to the syringe barrel. The cap may be moved in spring-biased contact along the needle body and beyond its tip whereupon it springs into alignment with the tip. By moving the cap in the reverse direction the tip becomes sealed therein.

18 Claims, 2 Drawing Sheets

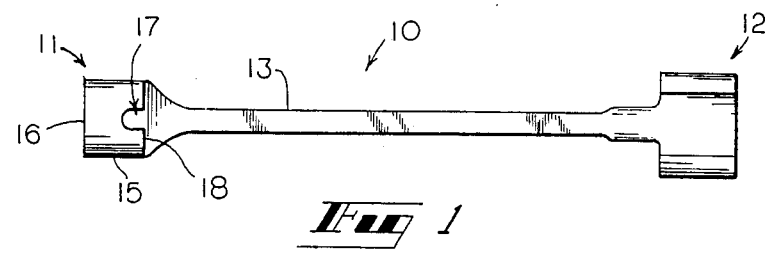
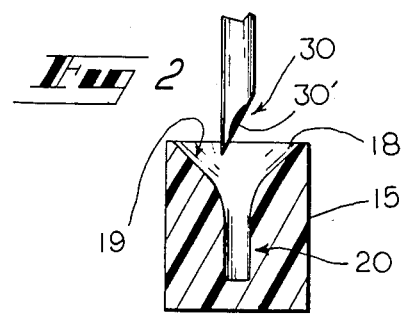
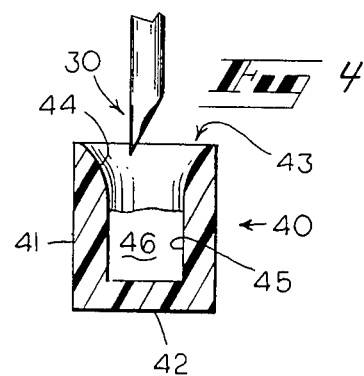
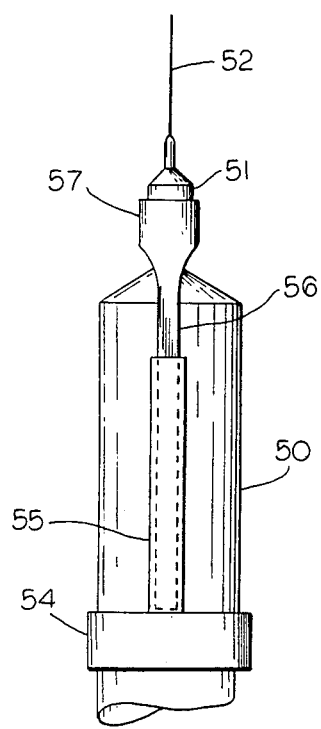
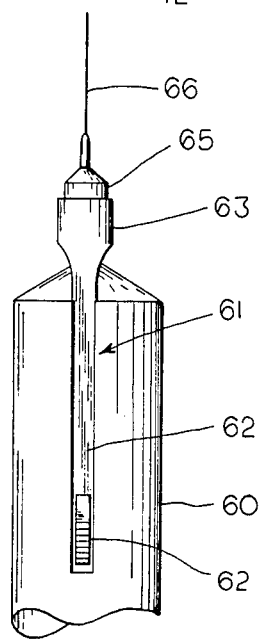

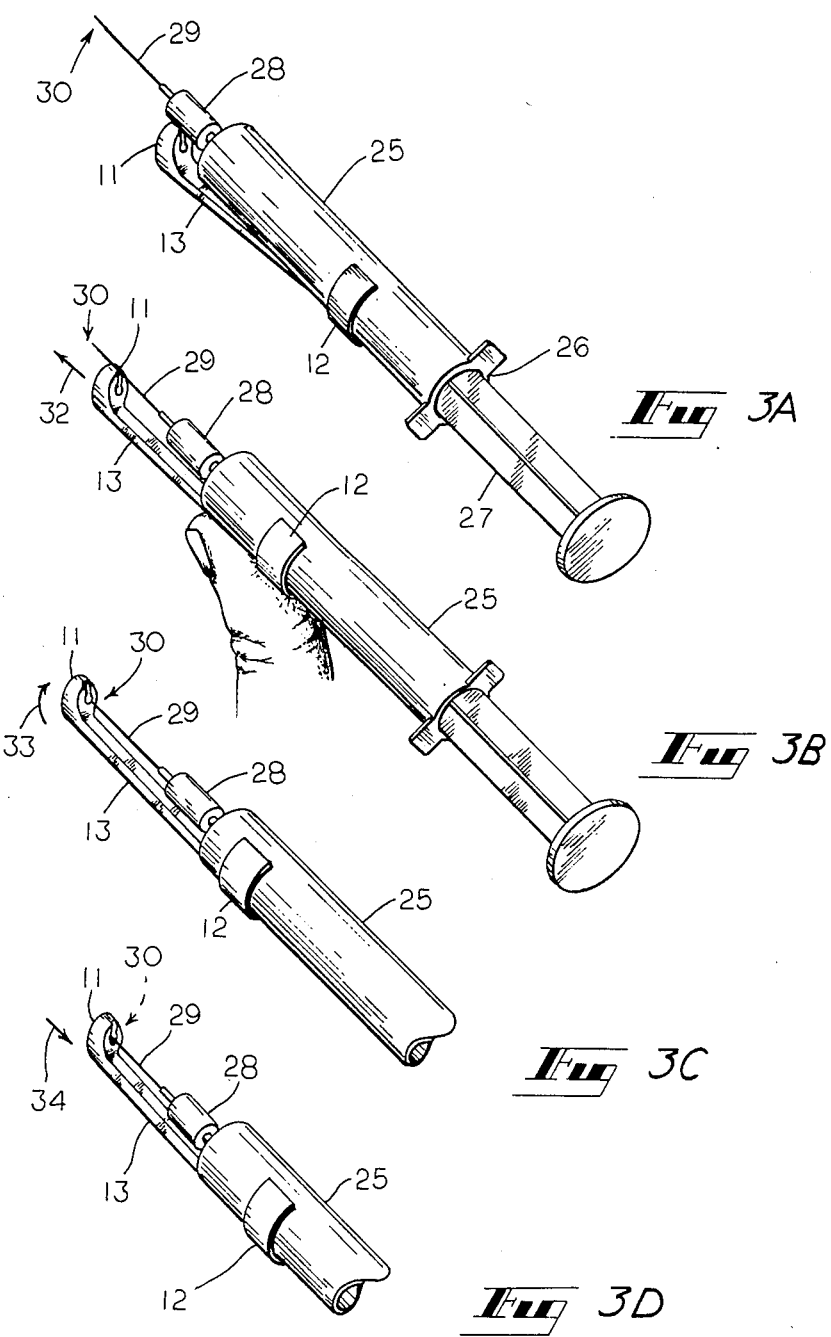

SYRINGE SEALING DEVICE AND METHOD

TECHNICAL FIELD

This invention relates generally to syringes, and particularly to methods and devices for sealing syringes.

BACKGROUND OF THE INVENTION

Syringes are commonly used both to inject medications into patients as well as to obtain specimens of body fluids such as anaerobic blood samples. Often the tip of the syringe needle needs to be sealed. For example, once blood has been drawn into a syringe and removed from the patient's skin, the needle tip is commonly sealed immediately to prevent air contamination and then placed in ice pending subsequent laboratory examination and analysis of the blood sample. The needle tip has commonly been sealed by injecting it into a cork stopper. This tip sealing method has not worked well due to the difficulty of injecting the needle into a small cork with one hand while the other hand applies pressure to the skin injection site of the patient. Sealing has also been attempted into silicone filled caps. This too has not worked well and indeed is not often done.

Today there are substantial dangers associated with the use of syringes to obtain body fluids. For example, the syringe users sometimes prick or inject themselves by accident due to difficulty of sealing the needle tips with one hand otherwise occupied. Where such occurs there is a possibility that a serious disease may be transmitted from the patient to the nurse or other medical personnel using the syringe. Thus, in attempting to seal the tip of a syringe needle as by injecting it quickly into a cork stopper the needle may slip and puncture the skin of the nurse thereby possibly transmitting a disease.

Therefore, it is seen that an improved device and method for sealing syringes is needed today. It is to the provision of such that the present invention is primarily directed.

SUMMARY OF THE INVENTION

In one form of the invention a syringe sealing device comprises a cap having an interior portion of a size and shape for sealing a tip-end portion of a syringe needle in which portion a needle orifice is located. The device also has means for mounting the cap to the barrel portion of the syringe for movement of the cap between a non-sealing position spaced from the needle tip and a sealing position located about the needle tip.

In another form of the invention a device is provided for sealing a syringe of the type having a tubular needle formed with an orifice adjacent a needle tip which needle is mounted to an elongated syringe barrel with the interior of the tubular needle in fluid communication with an interior portion of the barrel in which a plunger is movably positioned. The device comprises an elongated shank and cup-shaped means for sealing the needle tip mounted to one end of the elongated shank. Means are also provided for slidably mounting the other end of the shank to the syringe barrel.

In another form of the invention a sealable syringe comprises a barrel and a tubular needle mounted to the barrel that has a tip formed with an orifice on an end of an elongated needle body. The syringe also has means for sealing the needle tip orifice that includes a cap and means for coupled the cap with the barrel for cap movement between a position spaced from the needle tip and a position covered the needle tip.

In yet another form of the invention a sealable syringe comprises a barrel and a tubular needle mounted to the barrel with the needle having a tip portion that merges with an elongated body portion. A cap is provided having an interior cavity or bore into which the needle tip may be inserted and sealed. Means are also provided for mounting the cap for movement between a position spaced from the needle tip in spring-biased slidable contact with the elongated needle body and a position about the needle tip.

In still another form of the invention a method is provided for sealing the tip of a needle of a syringe of the type having a sealing cap movably mounted beside and in spring-biased contact with the syringe needle. The method comprises the steps of sliding the cap in spring-biased contact with the needle along the body of the needle in one direction to a position beyond the needle tip whereupon the cap springs into a position aligned with the needle. The cap is then moved in the reverse direction so as to bring it into sealing engagement about the needle tip.

BRIEF DESCRIPTION OF THE DRAWING

FIG. 1 is a side elevational view of a syringe sealing device that embodies principles of the invention in a preferred form.

FIG. 2 is a cross-sectional view of the cap portion of the syringe sealing device shown in FIG. 1 with the tip of a syringe needle positioned for entry into sealing engagement with the cap.

FIGS. 3A–3D are perspective views of a syringe with the sealing device of FIG. 1 mounted thereto which show a sequence of relative positions of the sealing device with respect to the syringe as it is used during a sealing operation in accordance with a method of the invention.

FIG. 4 is a cross-sectional view of a sealing device cap portion that embodies principles of the invention in alternative form.

FIG. 5 is an side elevational view of a portion of a syringe to which a sealing device is mounted that embodies principles of the invention in an alternative form.

FIG. 6 is a side elevational view of a portion of a syringe to which a sealing device is mounted that embodies principles of the invention in yet another form.

DETAILED DESCRIPTION

With reference next to the drawing, there is shown in FIG. 1 a syringe sealing device 10 of unitary plastic construction which includes a cup-shaped cap 11 which is connected to a collar 12 by means of an elongated, substantially straight shank 13. The sealing cap 11 as illustrated in FIGS. 1–3 has a generally cylindrical exterior side surface 15 and a flat end wall 16. A portion of the side wall 15 is seen to be coextensive with the elongated shank 13 while another portion is formed with a notch 17 that extends to a hollow cylindrical entry 18. The interior of the plastic cap is shaped like a funnel to include a conical portion 19 and a cylindrical portion 20. The conical portion is designed to serve as a means for guiding the tip of a needle into the interior or bore of the cap while the cylindrical portion is designed to seal the tip of a needle in which a needle orifice is located. The resilient clip-on type collar 12 is of an arcuate, generally semi-cylindrical shape. It is sized to grip the cylindrical side of a syringe barrel securely to a degree such that it may be manually forced to slide along the barrel while otherwise snuggly maintaining its longitudinal position along the barrel.

With reference next to FIGS. 3A–3D a syringe is shown having a hollow cylindrical barrel 25 formed with an opening at one end 26 through which a push rod 27 extends to ambiance. An unshown plunger is mounted to the end of the push rod 27 located within the barrel 25. A needle coupler 28 extends from the other end of the barrel from which a thin, hollow needle 29 in turn extends to a beveled needle tip 30 in which an orifice 30' is formed. Thusly described, the syringe is of conventional construction.

The syringe sealing device 10 is shown in FIG. 3A mounted to the syringe with its resilient collar 12 snapped onto the side of the barrel 25 and with the cap 11 spring biased against the side of the coupler 28. The inherent resilience of the plastic device 10 enables the collar to be spread as it is forced onto the barrel and then to grip the barrel surface. Since the cap 11 is distended from its normally relaxed position shown in FIG. 1, where it is generally aligned with the collar 12, it is spring biased against the side of the coupler. In this position it is seen that the needle tip 30 is exposed so that it may be injected into a patient as, for example, to withdraw a body fluid such as blood by manual actuation of the push rod 27.

FIGS. 3B–3D show a sequence of steps taken in using the syringe sealing device 10. These steps are taken once the syringe itself has been used in its conventional manner in withdrawing a body fluid. During that event the needle and its tip are fully exposed with the presence of the sealing device provides no interference. Once a body fluid sample has been drawn into the syringe the cap 11 is slid along and in direct contact with the coupler 28 and then along the elongaged body position of the needle 29. This is shown being done in FIG. 3B by the thumb of the syringe operator pushing against the shank 13 and the collar 12. As the sealing device is moved in the direction of arrow 32, direct sliding contact is maintained between a side of the cap and the body of the needle by the inherent resiliency of the device. The presence of notch 17 aids in guiding the cap along the needle. This movement is continued until the cap 11 moves beyond and therefore out of direct contact with the tip 30 of the needle as shown in FIG. 3C. This is of course made possible by the shank being longer than the exposed portion of the needle. Once this occurs the cap springs to its natural unbiased position generally aligned with the the collar 12 as shown being done by arrow 33. The cap 11 is beyond but now aligned with the needle tip.

Finally, the device is moved in the reverse direction shown by arrow 34 by the thumb pressed against the device shank and collar thereby causing the cap 11 to move over and about the needle tip 30. When this is done the needle tip is brought against the conical interior portion 19 of the cap and then guided into the cylindrical portion 20 which, being slightly smaller than the needle tip, closes and seals the orifice 30'. Depending on the degree of hardness of the plastic of which the device is preferably made, and the manual force employed, the tip of the needle may be driven either not quite to the bottom of the cylindrical portion 20, or to the bottom, or even beyond the bottom and into the plastic. The resilient walls of portion 20 expand to receive the needle tip and then firmly engage it to seal the orifice 30' from ambiance.

The sealed syringe may now be handled without fear of contamination of the fluid held therewithin. Where the fluid is blood it is commonly submerged into an ice bath for later immergency and examination. It should be noted that during the procedure the operator's finger at no time comes into close proximity with the needle tip. Furthermore, the sealing device need not be removed from the conventional portion of the syringe at any time.

FIG. 4 shows an alternative form of the cap portion of the sealing device. Here, a cap 40 is seen to have an annular side 41 closed by an end wall 42 and an open end wall 43. Again, the interior of the cap has a generally conical or flared side wall 44 that merges with a substantially cylindrical portion 45. The diameter of the cylindrical portion 45 here however is greater than the diameter of a needle tip that it is to seal. Instead, the cylindrical portion 45 is filled with a pliant sealant material 46 of a puddy-like consistency in which a needle tip may be embedded so as to seal its orifice.

With reference next to FIG. 5 an alternative form of the invention is shown for use with a conventional syringe that has a cylindrical barrel 50 from which a coupler 51 and needle 52 extend. The sealing device here comprises a mounting collar or clip 54 that is fixedly, instead of slidably, secured about the barrel. A tube or channel 55 extends from the collar. A tongue 56 is telescopically received within the channel 55 to the end of which tongue a cap portion 57 is mounted as previously described. The channel and tongue thus effectively provide a 2-piece shank. In FIG. 5 the cap is shown spring biased against the coupler 51 as in the case in FIG. 3A. In use the cap is manually slid against the coupler and then the needle body until it is again passing the tip of the needle and springs into a position aligned with the needle tip. The direction of movement of the cap is then reversed causing the tip to become sealed therein. Throughout this operation the collar 54 remains fixed in its permanent position about the barrel.

In FIG. 6 yet another example of the invention is shown wherein the syringe is not of conventional construction but rather is slightly modified. Specifically, the syringe has a barrel 60 formed with a surface groove or open channel indicated at 61. An elongated shank 62 of a sealing device is slidably positioned within the groove. A trigger or thumb guide 62 projects from the shank out of the groove while lips of the channel overhang side edge portions of the shank so as to hold it slidably within the bounds of the channel. Again, the shank merges with a sealing cap 63 which is shown in spring-biased contact against the side of a coupler 65. In use, the shank is urged by thumb action so as to cause the cap 63 to slide in spring biased contact over the coupler 65 and then over the body of a needle 66 to a point just beyond the needle tip whereupon the cap springs into alignment with the tip. By then moving the cap in the reverse direction the tip of the needle is injected into sealing engagement with the interior or bore of the cap.

Although the cap has been shown fixed to a substantially straight shank in each example, this is not necessarily required. For example, the cap could be made to swivel upon the end of the shank so as to align it with the needle tip. The shank may also be arcuate or bowed which shape aids in providing the biasing force. Thus, it should be understood that the embodiments specifically described merely illustrate principles of the invention in preferred forms. Many modifications, additions and deletions other than those expressly mentioned may be made thereto without departure from the spirit and scope of the invention as set forth in the following claims.

We claim:

1. A device for sealing a syringe of the type having a tubular needle formed with an orifice adjacent a needle tip that is mounted to an elongated syringe barrel with the interior of the tubular needle in fluid communication with an interior portion of the barrel in which a plunger is movably positioned, and with the device comprising an elongated shank slidably mounted at one end to said barrel by a mounting means, said shank at the other end having a cup-shaped means fixed thereon to slidably receive the needle tip in a sealing engagement of said needle tip orifice.

2. The sealing device of claim 1 of unitary, plastic construction.

3. The sealing device of claim 1 wherein said mounting means comprises an arcuate resilient collar adapted to be snapped onto the barrel.

4. The sealing device of claim 3 wherein said cup-shaped means and said collar both extend to one common side of said shank.

5. The sealing device of claim 1 wherein said shank is resilient.

6. The sealing device of claim 1 wherein said cup-shaped means has a bore oriented generally parallel with said elongated shank.

7. The sealing device of claim 6 wherein said channel has a generally conical needle tip guiding portion that merges with a generally cylindrical needle tip orifice sealing portion.

8. The sealing device of claim 1 wherein at least a portion of said cup-shaped means is at least partially filled with a pliable sealant.

9. A syringe sealing device comprising a cap having an interior portion of a size and shape for sealing a tip-end portion of a syringe needle in which portion a needle orifice is located, and means located adjacent an open end of said cap for mounting the cap to the barrel portion of the syringe for movement of the cap between a non-sealing position spaced from the needle tip and a sealing position located about the needle tip, and wherein said mounting means is configured to be slidably mounted about the barrel and comprises an arcuate resilient collar and a resilient shank that extends from said collar to said cap.

10. The sealing device of claim 9 wherein said shank is substantially straight.

11. A sealable syringe comprising a barrel, a tubular needle mounted to one end of said barrel and which has a tip formed with an orifice on an end of an elongated needle body, and means for sealing said needle tip orifice that includes a cap and means for coupling said cap with said barrel for cap movement between a position spaced from said needle tip and a position covering said needle tip, and wherein said coupling means comprises a resilient collar slidably mounted about said barrel and an elongated, resilient shank that extends between said cap and said collar.

12. A sealable syringe comprising a barrel, a tubular needle mounted to one end of said barrel and which has a tip formed with an orifice on an end of an elongated needle body, and means for sealing said needle tip orifice that includes a cap and means for coupling said cap with said barrel for cap movement between a position spaced from said needle tip and a position covering said needle tip, and wherein said coupling means comprises a shank that has two sections mounted for telescopic movement relative to each other with one section being fixedly mounted to said barrel along a parallel axis to the barrel and the other section fixedly mounted to said cap whereby the cap may receive the needle tip and may be moved with respect to said barrel.

13. A sealable syringe comprising a barrel formed with an elongated channel, a tubular needle mounted to one end of said barrel which has a tip formed with an orifice on an end of an elongated needle body, and means for sealing said needle tip orifice that includes a cap and means for coupling said cap with said barrel for cap movement between a position spaced from said needle tip and a position covering said needle tip, and wherein said coupling means includes an elongated shank slidably mounted in said barrel channel.

14. A sealable syringe comprising a barrel, a tubular needle mounted to said barrel with said needle having a tip portion that merges with an elongated body portion, a cap having a bore into which said needle tip may be inserted and sealed, and means for mounting said cap for movement between a position spaced from said needle tip in spring-biased slidable contact with said elongated needle body and a position about said needle tip.

15. The sealable syringe of claim 14 wherein the exterior surface of said barrel is generally cylindrical.

16. The sealable syringe of claim 15 wherein said mounting means comprises an arcuate collar located from said cap a distance greater than the spacing of said needle tip from said barrel, said collar being slidably mounted about said barrel.

17. The sealable syringe of claim 16 wherein said mounting means further comprises an elongated, resilient shank of a length longer than said needle that extends from said collar to said cap.

18. A method of sealing the tip of a needle of a syringe of the type having a sealing cap movably mounted beside and in spring-biased contact with the syringe needle provided by spring means attached to the cap comprising the steps of sliding the cap in spring-biased contact with the needle along the body of the needle in one direction to a position beyond the needle tip whereupon the cap springs into a position aligned with the needle, and moving the cap in the reverse direction so as to bring it into sealing engagement about the needle tip.

* * * * *